(12) United States Patent
Pinchuk et al.

(10) Patent No.: US 6,545,097 B2
(45) Date of Patent: Apr. 8, 2003

(54) DRUG DELIVERY COMPOSITIONS AND MEDICAL DEVICES CONTAINING BLOCK COPOLYMER

(75) Inventors: Leonard Pinchuk, Miami, FL (US); Sepideh Nott, Weston, MA (US); Marlene Schwarz, Newton, MA (US); Kalpana Kamath, Natick, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/734,639

(22) Filed: Dec. 12, 2000

(65) Prior Publication Data

US 2002/0107330 A1 Aug. 8, 2002

(51) Int. Cl.$^7$ .................. C08L 23/00; C08L 23/04; A61K 9/22
(52) U.S. Cl. .............. 525/240; 525/242; 525/221; 424/501; 424/423
(58) Field of Search ................. 525/240, 242, 525/221, 937; 424/501, 423

(56) References Cited

U.S. PATENT DOCUMENTS

| | | | |
|---|---|---|---|
| 4,276,394 A | 6/1981 | Kennedy et al. | 525/245 |
| 4,316,973 A | 2/1982 | Kennedy | 525/335 |
| 4,342,849 A | 8/1982 | Kennedy | 525/333.7 |
| 4,910,321 A | 3/1990 | Kennedy et al. | 549/213 |
| 4,929,683 A | 5/1990 | Kennedy et al. | 525/268 |
| 4,946,899 A | 8/1990 | Kennedy et al. | 525/244 |
| 5,066,730 A | 11/1991 | Kennedy et al. | 525/319 |
| 5,100,992 A * | 3/1992 | Cohn et al. | 528/26 |
| 5,122,572 A | 6/1992 | Kennedy et al. | 525/314 |
| RE34,640 E | 6/1994 | Kennedy et al. | 525/244 |
| 5,616,608 A | 4/1997 | Kinsella et al. | 514/449 |
| 5,716,981 A | 2/1998 | Hunter et al. | 514/449 |
| 5,733,925 A | 3/1998 | Kunz et al. | 514/449 |
| 5,741,331 A | 4/1998 | Pinchuk | 623/11 |
| 5,879,697 A | 3/1999 | Ding et al. | 424/422 |
| 5,900,246 A | 5/1999 | Lambert | 424/429 |
| 5,980,972 A | 11/1999 | Ding | 427/2.24 |
| 6,197,240 B1 * | 3/2001 | Pinchuk | 264/309 |
| 6,303,697 B1 * | 10/2001 | Yuan et al. | 528/328 |

FOREIGN PATENT DOCUMENTS

| | | |
|---|---|---|
| JP | 002211137 | 7/1981 |
| JP | 002211135 | 11/1990 |
| JP | 002211136 | 7/1994 |
| WO | WO 00/62830 | 10/2000 ........ A61L/27/00 |

OTHER PUBLICATIONS

Gyor et al., "Polyisobutylene–Based Thermoplastic Elastomers. I. Synthesis and Characterization of Polystyrene–Polyisobutylene–Polystyrene Triblock Copolymers," J.M.S.–Pure Appl. Chem., A31(12), pp. 2055–2065 (1994).
Pinchuk et al., "A New Family of Thermoplastic Elastomers for Ultra–Long Term Implant Based Upon a Backbone of Alternating Quaternary and Secondary Carbons," 24th Annual Meeting of the Society for Biomaterials, Apr. 22–26, 1998, San Diego, CA, p. 173.
Shinichi Terada et al., "Experimental Study of Ectopic–Free Tissue Transfer of Rabbit Epigastric Flap Using Small–Caliber Vascular Grafts," *Journal of Biomedical Materials Research*, vol. 45, No. 1, Apr. 1999, pp. 28–35.

\* cited by examiner

*Primary Examiner*—Nathan M. Nutter
*Assistant Examiner*—Olga Asinovsky
(74) *Attorney, Agent, or Firm*—Mayer Fortkort & Williams, PC; David B. Bonham, Esq.

(57) ABSTRACT

A composition for delivery of a therapeutic agent is provided. The composition comprises: (a) a biocompatible block copolymer comprising one or more elastomeric blocks and one or more thermoplastic blocks and (b) a therapeutic agent, wherein the block copolymer is loaded with the therapeutic agent. The block copolymer is preferably of the formula X—(AB)$_n$, where A is an elastomeric block, B is a thermoplastic block, n is a positive whole number and X is a seed molecule. The elastomeric blocks are preferably polyolefin blocks, and the thermoplastic blocks are preferably selected from vinyl aromatic blocks and methacrylate blocks. According to another aspect of the invention, a medical device is provided, at least a portion of which is insertable or implantable into the body of a patient. The medical device comprises (a) the above biocompatible block copolymer and (b) a therapeutic agent, wherein the block copolymer is loaded with the therapeutic agent. According to another aspect of the present invention, a method of treatment is provided in which the above device is implanted or inserted into a patient, resulting in the release of therapeutic agent in the patient over an extended period. According to yet another aspect of the invention, a coated medical device is provided which comprises: (a) an intravascular or intervascular medical device and (b) a coating over at least a portion of the intravascular or intervascular a medical device, wherein the coating comprises the above biocompatible block copolymer.

59 Claims, 5 Drawing Sheets

DRUG DELIVERY COMPOSITIONS AND MEDICAL DEVICES CONTAINING BLOCK COPOLYMER

FIELD OF THE INVENTION

The present invention relates to compositions for therapeutic agent delivery comprising a therapeutic-agent-loaded block copolymer. The present invention also relates to biocompatible block copolymer materials for use in connection with intravascular or intervascular medical devices.

BACKGROUND AND SUMMARY OF THE INVENTION

Polymers that release drug upon implantation or insertion into the body are known. However, a need remains in the art for a polymer that is effective for drug-release, while at the same time having good mechanical integrity and biocompatibility.

It is also known to use polymers in connection with implantable or insertable medical devices. However, such polymers frequently elicit a vigorous immune or foreign body response. This is particularly true of intravascular or intervascular medical devices, which commonly suffer from the consequences of inflammation and neointimal thickening after placement within the vasculature.

The above and other needs in the prior art have been met by the present invention. According to one aspect of the invention, a composition for delivery of a therapeutic agent is provided, which comprises: (a) a biocompatible block copolymer comprising one or more elastomeric blocks and one or more thermoplastic blocks and (b) a therapeutic agent, wherein the block copolymer is loaded with the therapeutic agent.

Numerous therapeutic agents are appropriate for use in connection with the present invention including anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, agents that interfere with endogenous vascoactive mechanisms, and combinations thereof. One specific example of a therapeutic agent is paclitaxel. The loaded block copolymer preferably comprises 0.1 to 70 wt % therapeutic agent.

Regarding the polymer configuration, the block copolymer is preferably of the formula X—(AB)$_n$, where A is an elastomeric block, B is a thermoplastic block, n is a positive whole number and X is a seed molecule.

Regarding the blocks within the copolymer, the elastomeric blocks are preferably polyolefin blocks. More preferably, the polyolefin blocks are of the general formula —(CRR'—CH$_2$)$_n$—, where R and R' are linear or branched aliphatic groups or cyclic aliphatic groups. Even more preferably, the polyolefin blocks are polyisobutylene blocks. The amount of polyolefin blocks preferably ranges from between 95 and 45 mol % of the block copolymer.

The thermoplastic blocks are preferably selected from vinyl aromatic blocks and methacrylate blocks. The methacrylate blocks are preferably selected from methylmethacrylate, ethylmethacrylate and hydroxyethyl methacrylate monomers, as well as blocks of mixtures of these monomers. The vinyl aromatic polymer blocks are preferably selected from blocks of styrene and α-methylstyrene, as well as blocks of mixtures of these monomers.

The molecular weight of the block copolymer preferably ranges from 80,000 to 300,000 Daltons. In some embodiments, the molecular weight of the polyolefin blocks preferably ranges from 60,000 to 200,000 Daltons, and the molecular weight of the vinyl aromatic polymer blocks preferably ranges from 20,000 to 100,000 Daltons.

According to another aspect of the present invention, a medical device is provided, at least a portion of which is insertable or implantable into the body of a patient. The medical device comprises (a) the above block copolymer and (b) a therapeutic agent, wherein the block copolymer is loaded with the therapeutic agent.

In some embodiments, only a portion of the medical device comprises the block copolymer. As an example, the portion of the medical device can be in the form of a coating on the medical device. Preferred coating dimensions are 0.1 to 50 microns in thickness.

Preferably, the therapeutic agent is released over an extended period after implantation in a patient.

Preferred sites for implantation or insertion of the medical device are the coronary vasculature, peripheral vasculature, esophagus, trachea, colon, gastrointestinal tract, biliary tract, urinary tract, prostate and brain.

In some embodiments, the medical device is adapted such that at least a portion of the block copolymer is exposed to bodily fluid upon insertion or implantation in the body. In others, the medical device is adapted to expose at least a portion of the block copolymer to tissue such as solid tissue.

Preferred medical devices include catheters, guide wires, balloons, filters, stents, stent grafts, vascular grafts, vascular patches, shunts and intraluminal paving systems. In some embodiments, the medical device is provided with a sheath for covering the block copolymer during insertion into the body to prevent premature therapeutic agent release.

In certain embodiments, the medical device further comprises a polymer or copolymer of one or more of the following: a polycarboxylic acid, a cellulose acetate polymer, a cellulose nitrate polymer, a gelatin, a polyvinylpyrrolidone, a cross-linked polyvinylpyrrolidone, a polyanhydride, a polyamide, a polyvinyl alcohol, a polyvinyl ether, a polyvinyl aromatic, a polyethylene oxide, a glycosaminoglycan, a polysaccharide, a polyester, a polyacrylamide, a polyether, a polyether sulfone, a polycarbonate, a polyalkylene, a halogenated polyalkylene, a polyurethane, a polyorthoester, a polypeptide, a silicone, a siloxane polymer, a polylactic acid, a polyglycolic acid, a polycaprolactone, a polyhydroxybutyrate valerate, a fibrin, a collagen, a collagen derivative or a hyaluronic acid. Particularly preferred polymers and copolymers are polyacrylic acids, ethylene-vinyl acetate copolymers, and copolymers of polylactic acid and polycaprolactone.

Such polymers or copolymers can be blended with the biocompatible block copolymer, or they can be provided in a layer that does not contain the biocompatible block copolymer.

According to another aspect of the present invention, a method of treatment is provided in which the above device is implanted or inserted into a patient, resulting in the release of therapeutic agent in the patient over an extended period of time.

According to yet another aspect of the invention, a coated medical device is provided which comprises: (a) an intravascular or intervascular medical device; and (b) a coating over at least a portion of the intravascular or intervascular medical device, the coating comprising the above biocompatible block copolymer. Preferred intravascular or intervascular medical devices for this aspect of the invention include balloons, stents, stent grafts, vascular grafts, vascular patches, shunts, catheters and filters.

One advantage of the present invention is that it provides a polymer-based drug delivery composition with good mechanical integrity.

Another advantage is that a polymer-based drug delivery composition can be provided that has good biocompatibility.

Another advantage of the present invention is that medical devices can be provided that, upon placement in the vasculature, result in reduced inflammation and neointimal thickening relative to other traditionally used polymeric materials.

Still other embodiments and advantages will become readily apparent to those skilled in the art upon review of the Specification and claims to follow.

DETAILED DESCRIPTION OF THE INVENTION

Figure 1:
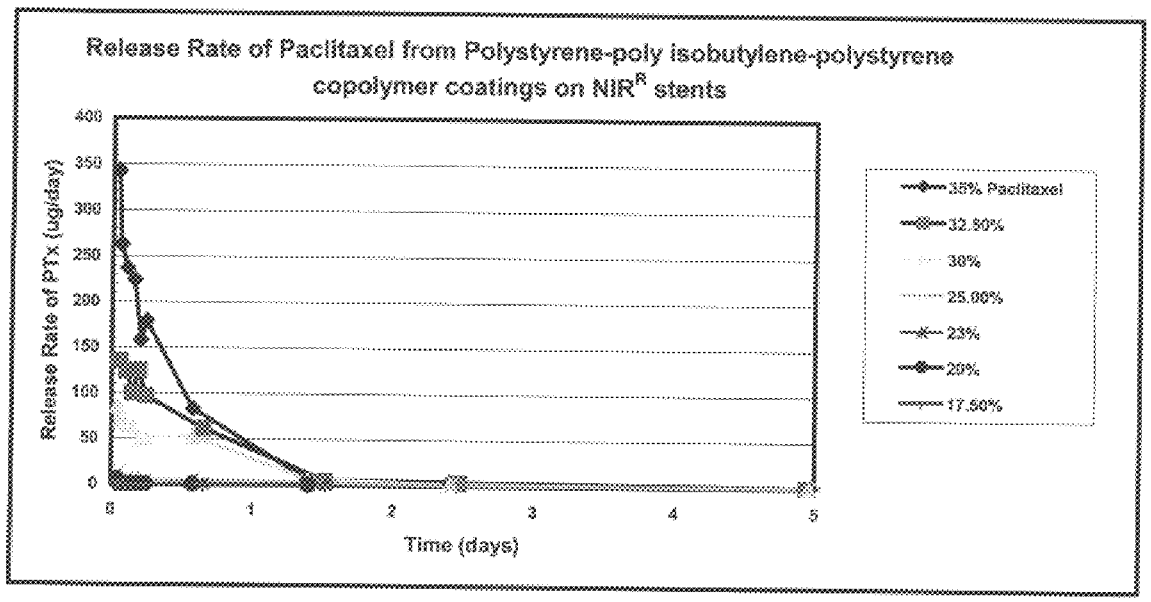
FIG. 1 illustrates release rate as a function of time for stents coated with polystyrene-polyisobutylene-polystyrene copolymer and paclitaxel in varying ratios.
Figure 2A:
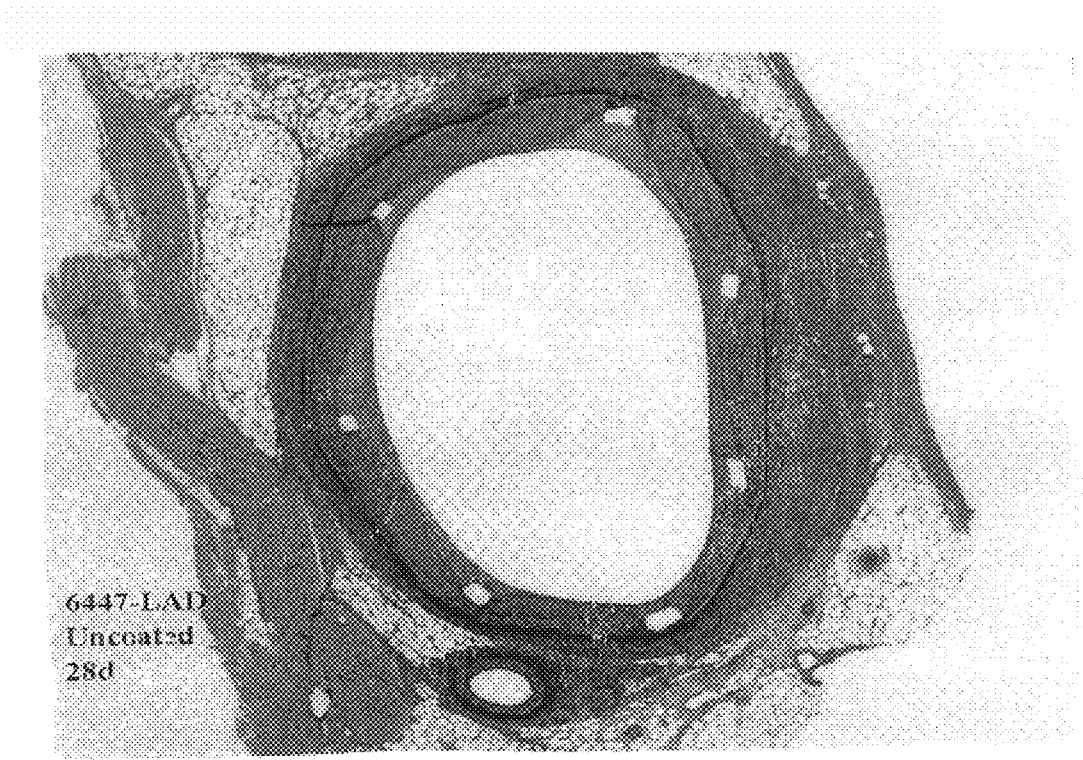
FIGS. 2A–2D are photographs, after 28 days in a porcine coronary artery, of (1) a bare stainless steel stent, (2) a stainless steel stent with a coating of traditional "biostable" polyurethane polymer, (3) a stainless steel stent with a coating of a traditional "biodegradable" copolymer of polylactic acid ("PLA") and polyglycolic acid ("PGA") and (4) a stainless steel stent covered with a coating of polystyrene-polyisobutylene-polystyrene copolymer in accordance with an embodiment of the present invention.
Figure 2B:
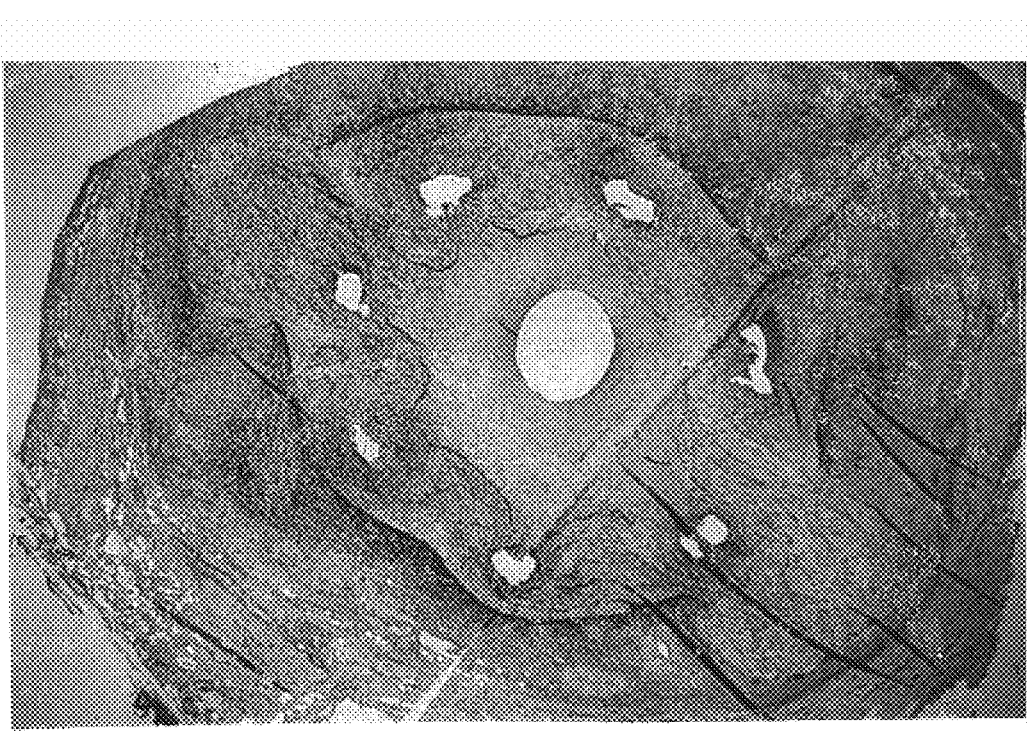
Figure 2C:
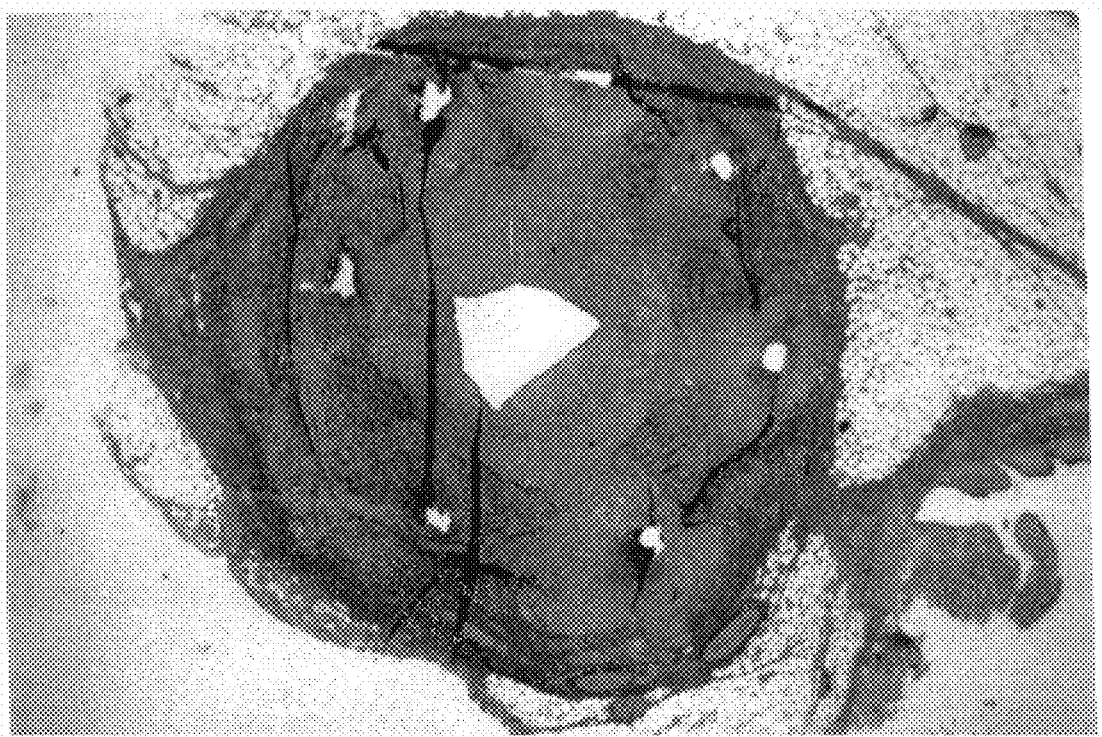
Figure 2D:
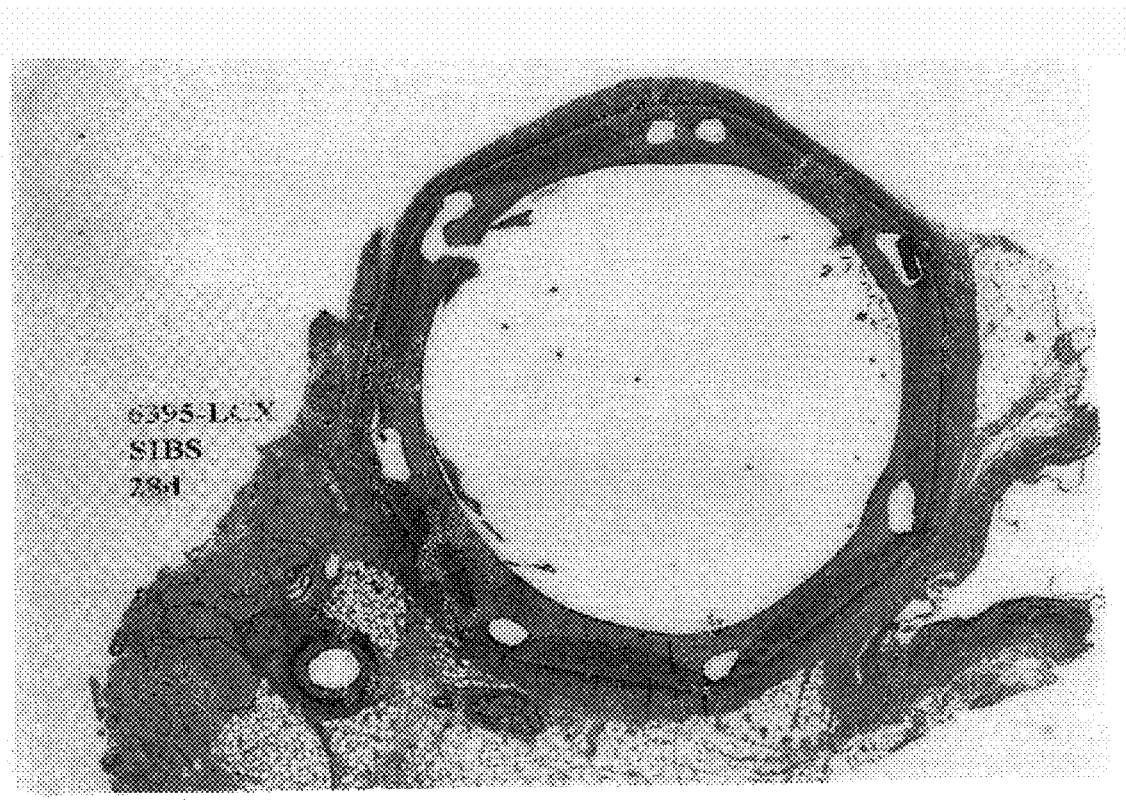

The present invention relates to compositions comprising a therapeutic-agent-loaded block copolymer that are useful for delivery of a therapeutic agent and to biocompatible block copolymer materials useful, for example, in connection with intravascular or intervascular medical devices.

Block copolymers suitable for the practice of the present invention preferably have a first elastomeric block and a second thermoplastic block. More preferably, the block copolymers have a central elastomeric block and thermoplastic end blocks. Even more preferably, such block copolymers have the general structure:

(a) BAB or ABA (linear triblock),
(b) B(AB)$_n$ or A(BA)$_n$ (linear alternating block), or
(c) X—(AB)$_n$ or X—(BA)$_n$ (includes diblock, triblock and other radial block copolymers), where A is an elastomeric block, B is a thermoplastic block, n is a positive whole number and X is a starting seed molecule.

Most preferred are X—(AB)$_n$ structures, which are frequently referred to as diblock copolymers and triblock copolymers where n=1 and n=2, respectively (this terminology disregards the presence of the starting seed molecule, for example, treating A—X—A as a single A block with the triblock therefore denoted as BAB). Where n=3 or more, these structures are commonly referred to as star-shaped block copolymers.

The A blocks are preferably soft elastomeric components which are based upon one or more polyolefins, more preferably a polyolefinic block having alternating quaternary and secondary carbons of the general formulation: —(CRR'—CH$_2$)$_n$—, where R and R' are linear or branched aliphatic groups such as methyl, ethyl, propyl, isopropyl, butyl, isobutyl and so forth, or cyclic aliphatic groups such as cyclohexane, cyclopentane, and the like, with and without pendant groups.

Polymers of isobutylene,

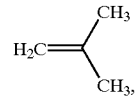

(i.e., polymers where R and R' are the same and are methyl groups) are most preferred.

The B blocks are preferably hard thermoplastic blocks that, when combined with the soft A blocks, are capable of, inter alia, altering or adjusting the hardness of the resulting copolymer to achieve a desired combination of qualities. Preferred B blocks are polymers of methacrylates or polymers of vinyl aromatics. More preferred B blocks are (a) made from monomers of styrene

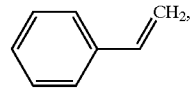

styrene derivatives (e.g., α-methylstyrene, ring-alkylated styrenes or ring-halogenated styrenes) or mixtures of the same or are (b) made from monomers of methylmethacrylate, ethylmethacrylate hydroxyethyl methacrylate or mixtures of the same.

The properties of the block copolymers used in connection with the present invention will depend upon the lengths of the A blocks and B blocks, as well as the relative amounts of each.

For example, the elastomeric properties of the block copolymer will depend on the length of the A block chains, with a weight average molecular weight of from about 2,000 to about 30,000 Daltons tending to produce rather inelastic products, and a weight average molecular weight of 40,000 Daltons or above tending to produce products that are more soft and rubbery. Hence, for purposes of the present invention, the combined molecular weight of the block copolymer is preferably in excess of 40,000 Daltons, more preferably in excess of 60,000 Daltons, and most preferably between about 90,000 to about 300,000 Daltons.

As another example, the hardness of the block copolymer is proportional to the relative amount of B blocks. In general, the copolymer has a preferred hardness that is between about Shore 20A and Shore 75D, and more preferably between about Shore 40A and Shore 90A. This result can be achieved by varying the proportions of the A and B blocks, with a lower relative proportion of B blocks resulting in a copolymer of lower hardness, and a higher relative proportion of B blocks resulting in a copolymer of higher hardness. As a specific example, high molecular weight (i.e., greater than 100,000 Daltons) polyisobutylene is a soft gummy material with a Shore hardness of approximately 10A. Polystyrene, is much harder, typically having a Shore hardness on the order of 100D. As a result, when blocks of polyisobutylene and styrene are combined, the resulting copolymer can have a range of hardnesses from as soft as Shore 10A to as hard as Shore 100D, depending upon the relative amounts of polystyrene and polyisobutylene. In general, to achieve a preferred hardness ranging from Shore 30A to Shore 90A, the amount of polystyrene ranges from between 2 and 25 mol %. More preferably, the preferred hardness ranges from Shore 35A to Shore 70A and the amount of polystyrene ranges from 5 to 20 mol %.

Polydispersity (i.e., the ratio of weight average molecular weight to number average molecular weight) gives an indication of the molecular weight distribution of the copolymer, with values significantly greater than 4 indicating a broad molecular weight distribution. The polydispersity has a value of one when all molecules within a sample are the same size. Typically, the copolymers for use in connection with the present invention have a relatively tight molecular weight distribution, with a polydispersity of about 1.1 to 1.7.

One advantage associated with the above-described copolymers is their high tensile strength. For example, the tensile strength of triblock copolymers of polystyrene-polyisobutylene-polystyrene frequently ranges from 2,000 to 4,000 psi or more.

Another advantage of such copolymers is their resistance to cracking and other forms of degradation under in vivo conditions. In addition, these polymers exhibit excellent biocompatibility, including vascular compatibility, as demonstrated by their tendency to provoke minimal adverse tissue reactions as demonstrated by reduced polymorphonuclear leukocyte and reduced macrophage activity. Still further, these polymers are generally hemocompatible as demonstrated by their ability to minimize thrombotic occlusion of small vessels as demonstrated by coating such copolymers on coronary stents. See Example 6 below.

The above-described block copolymers can be made using any appropriate method known in the art. A preferred process of making the block copolymers is by carbocationic polymerization involving an initial polymerization of a monomer or mixtures of monomers to form the A blocks, followed by the subsequent addition of a monomer or a mixture of monomers capable of forming the B blocks.

Such polymerization reactions can be found, for example, in Additional U.S. Pat. Nos. 4,276,394, 4,316,973, 4,342,849, 4,910,321, 4,929,683, 4,946,899, 5,066,730, 5,122,572 and/or Re. 34,640. Each of these patents is hereby incorporated by reference in its entirety.

The techniques disclosed in these patents generally involve a "catalyst starting molecule" (also referred to as "initiators", "telechelic starting molecules", "seed molecules" or "inifers"), which can be used to create X—(AB)$_n$ structures, where X is the catalyst starting molecule, and n can be 1, 2, 3 or more. As noted above, the resulting molecules are referred to as diblock copolymers where n is 1, triblock copolymers (disregarding the presence of the starting molecule) where n is 2, and star-shaped block copolymers where n is 3 or more.

In general, the polymerization reaction is conducted under conditions that minimize or avoid chain transfer and termination of the growing polymer chains. Steps are taken to keep active hydrogen atoms (water, alcohol and the like) to a minimum. The temperature for the polymerization is usually between $-10°$ and $-90°$ C., the preferred range being between $-60°$ and $-80°$ C., although lower temperatures may be employed if desired.

Preferably, one or more A blocks, for example, polyisobutylene blocks, are formed in a first step, followed by the addition of B blocks, for example, polystyrene blocks, at the ends of the A blocks.

More particularly, the first polymerization step is generally carried out in an appropriate solvent system, typically a mixture of polar and non-polar solvents such as methyl chloride and hexanes. The reaction bath typically contains:

the aforementioned solvent system, olefin monomer, such as isobutylene, an initiator (inifer or seed molecule) such as tert-ester, tert-ether, tert-hydroxyl or tert-halogen containing compounds, and more typically cumyl esters of hydrocarbon acids, alkyl cumyl ethers, cumyl halides and cumyl hydroxyl compounds as well as hindered versions of the above, a coinitiator, typically a Lewis Acid, such as boron trichloride or titanium tetrachloride.

Electron pair donors such as dimethyl acetamide, dimethyl sulfoxide, or dimethyl phthalate can be added to the solvent system. Additionally, proton-scavengers that scavenge water, such as 2,6-di-tert-butylpyridine, 4-methyl-2,6-di-tert-butylpyridine, 1,8-bis(dimethylamino)-naphthalene, or diisopropylethyl amine can be added.

The reaction is commenced by removing the tert-ester, tert-ether, tert-hydroxyl or tert-halogen (herein called the "tert-leaving groups") from the seed molecule by reacting it with the Lewis acid. In place of the tert-leaving groups is a quasi-stable or "living" cation which is stabilized by the surrounding tertiary carbons as well as the polar solvent system and electron pair donors. After obtaining the cation, the A block monomer, such as isobutylene, is introduced which cationically propagates or polymerizes from each cation on the seed molecule. When the A block is polymerized, the propagated cations remain on the ends of the A blocks. The B block monomer, such as styrene, is then introduced which polymerizes and propagates from the ends of the A block. Once the B blocks are polymerized, the reaction is terminated by adding a termination molecule such as methanol, water and the like.

As is normally the case, product molecular weights are determined by reaction time, reaction temperature, the nature and concentration of the reactants, and so forth. Consequently, different reaction conditions will produce different products. In general, synthesis of the desired reaction product is achieved by an iterative process in which the course of the reaction is monitored by the examination of samples taken periodically during the reaction—a technique widely employed in the art. To achieve the desired product, an additional reaction may be required in which reaction time and temperature, reactant concentration, and so forth are changed.

Additional details regarding cationic processes for making copolymers are found, for example, in U.S. Pat. Nos. 4,276,394, 4,316,973, 4,342,849, 4,910,321, 4,929,683, 4,946,899, 5,066,730, 5,122,572 and/or Re. 34,640.

The block copolymers described in the preceding paragraphs may be recovered from the reaction mixtures by any of the usual techniques including evaporation of solvent, precipitation with a non-solvent such as an alcohol or alcohol/acetone mixture, followed by drying, and so forth. In addition, purification of the copolymer can be performed by sequential extraction in aqueous media, both with and without the presence of various alcohols, ethers and ketones.

Once synthesized, the block copolymers can be used, for example, to provide therapeutic-agent-loaded block copolymer compositions for therapeutic agent delivery, or to provide biocompatible intravascular or intervascular devices.

For a given mode of administration, a wide variety of therapeutic agents, including genetic therapeutic agents, non-genetic therapeutic agents, and cells, can be used in conjunction with the block copolymers of the invention. Exemplary non-genetic therapeutic agents include:

anti-thrombotic agents such as heparin, heparin derivatives, urokinase, and PPack (dextrophenylalanine proline arginine chloromethylketone);

anti-inflammatory agents such as dexamethasone, prednisolone, corticosterone, budesonide, estrogen, sulfasalazine and mesalamine;

antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors;

anesthetic agents such as lidocaine, bupivacaine and ropivacaine;

anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides;

vascular cell growth promoters such as growth factors, transcriptional activators, and translational promotors;

vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

protein kinase and tyrosine kinase inhibitors (e.g., tyrphostins, genistein, quinoxalines);

prostacyclin analogs;

cholesterol-lowering agents;

angiopoietins;

antimicrobial agents such as triclosan, cephalosporins, aminoglycosides and nitrofurantoin;

cytotoxic agents, cytostatic agents and cell proliferation affectors;

vasodilating agents; and agents that interfere with endogenous vascoactive mechanisms.

Exemplary genetic therapeutic agents include:
anti-sense DNA and RNA;
DNA coding for:
  anti-sense RNA,
  tRNA or rRNA to replace defective or deficient endogenous molecules,
  angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor and insulin like growth factor,
  cell cycle inhibitors including CD inhibitors,
  thymidine kinase ("TK") and other agents useful for interfering with cell proliferation, and
  the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7.

These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Vectors of interest for delivery of genetic therapeutic agents include
  Plasmids
  Viral vectors such as adenovirus (AV), adenoassociated virus (AAV) and lentivirus
  Non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in U.S. Pat. No. 5,733,925 assigned to NeoRx Corporation, the entire disclosure of which is incorporated by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following

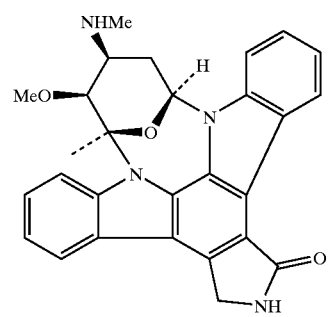

I formula, as well as diindoloalkaloids having one of the following general structures:

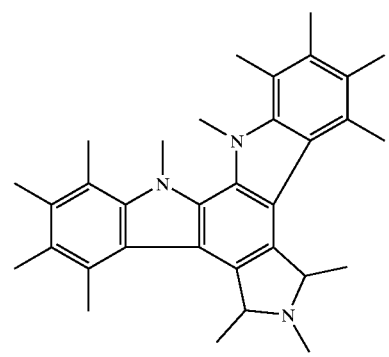

II

III

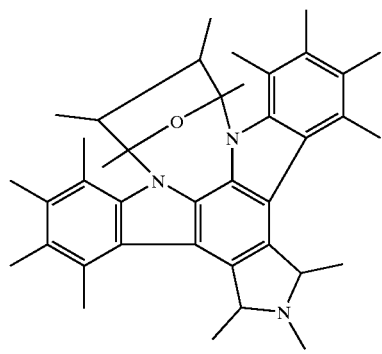

IV

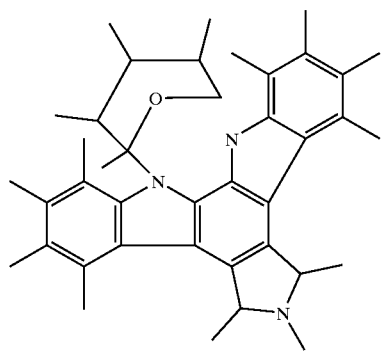

V

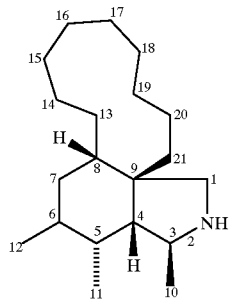

VI

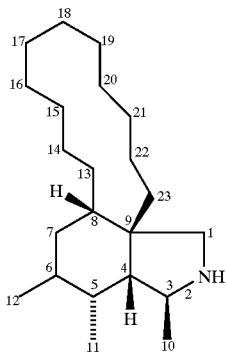

as well as stimulators of the production or activation of TGF-beta, including tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like.

Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit migration of vascular smooth muscle cells from the medial wall into the intima ("anti-migratory agents"). Several preferred examples are derived from phenylalanine (cytochalasins), tryptophan (chaetoglobosins), or leucine (aspochalasins), resulting in a benzyl, indol-3-yl methyl or isobutyl group, respectively, at position C-3 of a substituted perhydroisoindole-1-one moiety (Formula V or VI). The perhydroisoindole moiety in turn contains an 11-, 13- or 14-atom carbocyclic- or oxygen-containing ring linked to positions C-8 and C-9. All naturally occurring cytochalasins contain a methyl group at C-5; a methyl or methylene group at C-12; and a methyl group at C-14 or C-16. Exemplary molecules include cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D and the like, as well as functional equivalents and derivatives thereof. Certain cytochalasin derivatives are set forth in Japanese Patent Nos. 72 01,925; 72 14,219; 72 08,533; 72 23,394; 72 01924; and 72 04,164.

Other representative examples of anti-migratory agents include inhibitors (i.e., agonists and antagonists, and competitive or non-competitive inhibitors) of chemotactic factors and their receptors (e.g., complement chemotaxins such as C5a, C5a desarg or C4a; extracellular matrix factors, e.g., collagen degradation fragments), or of intracellular cytoskeletal proteins involved in locomotion (e.g., actin, cytoskeletal elements, and phosphatases and kinases involved in locomotion). Representative examples of useful therapeutic agents in this category of anti-migratory agents include: caffeic acid derivatives and nilvadipine (a calcium antagonist), and steroid hormones.

Agents that inhibit the intracellular increase in cell volume (i.e., the tissue volume occupied by a cell) such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents are appropriate for the practice of the present invention and include one or more of the following:

Ca-channel blockers including:
    Benzothiazapines such as diltiazem and clentiazem
    Dihydropyridines such as nifedipine, amlodipine and nicardapine
    Phenylalkylamines such as verapamil Serotonin pathway modulators including:
    5-HT antagonists such as ketanserin and naftidrofuryl
    5-HT uptake inhibitors such as fluoxetine Cyclic nucleotide pathway agents including:
    Phosphodiesterase inhibitors such as cilostazole and dipyridamole
    Adenylate/Guanylate cyclase stimulants such as forskolin
    Adenosine analogs Catecholamine modulators including:
    α-antagonists such as prazosin and bunazosine
    β-antagonists such as propranolol
    α/β-antagonists such as labetalol and carvedilol Endothelin receptor antagonists Nitric oxide donors/releasing molecules including:
    Organic nitrates/nitrites such as nitroglycerin, isosorbide dinitrate and amyl nitrite
    Inorganic nitroso compounds such as sodium nitroprusside
    Sydnonimines such as molsidomine and linsidomine
    Nonoates such as diazenium diolates and NO adducts of alkanediamines
    S-nitroso compounds including low molecular weight compounds (e.g., S-nitroso derivatives of captopril, glutathione and N-acetyl penicillamine), high molecular weight compounds (e.g., S-nitroso derivatives of proteins, peptides, oligosaccharides, polysaccharides, synthetic polymers/oligomers and natural polymers/oligomers)
    C-nitroso-, O-nitroso- and N-nitroso-compounds
    L-arginine ACE inhibitors such as cilazapril, fosinopril and enalapril ATII-receptor antagonists such as saralasin and losartin Platelet adhesion inhibitors such as albumin and polyethylene oxide Platelet aggregation inhibitors including:
    Aspirin and thienopyridine (ticlopidine, clopidogrel)
    GP IIb/IIIa inhibitors such as abciximab, epitifibatide and tirofiban Coagulation pathway modulators including:
    Heparinoids such as heparin, low molecular weight heparin, dextran sulfate and β-cyclodextrin tetradecasulfate
    Thrombin inhibitors such as hirudin, hirulog, PPACK(D-phe-L-propyl-L-arg-chloromethylketone) and argatroban
    FXa inhibitors such as antistatin and TAP (tick anticoagulant peptide)
    Vitamin K inhibitors such as warfarin
    Activated protein C Cyclooxygenase pathway inhibitors such as aspirin, ibuprofen, flurbiprofen, indomethacin and sulfinpyrazone Natural and synthetic corticosteroids such as dexamethasone, prednisolone, methprednisolone and hydrocortisone Lipoxygenase pathway inhibitors such as nordihydroguairetic acid and caffeic acid Leukotriene receptor antagonists Antagonists of E- and P-selectins Inhibitors of VCAM-1 and ICAM-1 interactions Prostaglandins and analogs thereof including:
    Prostaglandins such as PGE1 and PGI2
    Prostacyclin analogs such as ciprostene, epoprostenol, carbacyclin, iloprost and beraprost Macrophage activation preventers including bisphosphonates HMG-CoA reductase inhibitors such as lovastatin, pravastatin, fluvastatin, simvastatin and cerivastatin Fish oils and omega-3-fatty acids Free-radical scavengers/antioxidants such as probucol, vitamins C and E, ebselen, trans-retinoic acid and SOD mimics Agents affecting various growth factors including:
    FGF pathway agents such as bFGF antibodies and chimeric fusion proteins
    PDGF receptor antagonists such as trapidil
    IGF pathway agents including somatostatin analogs such as angiopeptin and ocreotide
    TGF-β pathway agents such as polyanionic agents (heparin, fucoidin), decorin, and TGF-β antibodies
    EGF pathway agents such as EGF antibodies, receptor antagonists and chimeric fusion proteins
    TNF-α pathway agents such as thalidomide and analogs thereof
    Thromboxane A2 (TXA2) pathway modulators such as sulotroban, vapiprost, dazoxiben and ridogrel Protein tyrosine kinase inhibitors such as tyrphostin, genistein and quinoxaline derivatives
MMP pathway inhibitors such as marimastat, ilomastat and metastat
Cell motility inhibitors such as cytochalasin B
Antiproliferative/antineoplastic agents including:
  Antimetabolites such as purine analogs(6-mercaptopurine), pyrimidine analogs (e.g., cytarabine and 5-fluorouracil) and methotrexate
  Nitrogen mustards, alkyl sulfonates, ethylenimines, antibiotics (e.g., daunorubicin, doxorubicin), nitrosoureas and cisplatin
  Agents affecting microtubule dynamics (e.g., vinblastine, vincristine, colchicine, paclitaxel and epothilone)
  Caspase activators
  Proteasome inhibitors
  Angiogenesis inhibitors (e.g., endostatin, angiostatin and squalamine)
  Rapamycin, cerivastatin, flavopiridol and suramin
Matrix deposition/organization pathway inhibitors such as halofuginone or other quinazolinone derivatives and tranilast
Endothelialization facilitators such as VEGF and RGD peptide
Blood rheology modulators such as pentoxifylline.

In addition, combinations of the above therapeutic agents can be used.

A wide range of therapeutic agent loadings can be used in connection with the above block copolymers, with the amount of loading being readily determined by those of ordinary skill in the art and ultimately depending upon the condition to be treated, the nature of the therapeutic agent itself, the means by which the therapeutic-agent-loaded copolymer is administered to the intended subject, and so forth. The loaded copolymer will frequently comprise from less than one to 70 wt % therapeutic agent.

In many preferred embodiments of the invention, the copolymer is used to provide (a) the entirety of a medical device or (b) a portion of a medical device (i.e., the copolymer is used as a "device or device portion"). Portions of medical devices for which the copolymers of the present invention find use include any fraction of a medical device, such as device coatings, device components and so forth.

In some instances, therapeutic agent is released from the device or device portion to a bodily tissue or bodily fluid upon contacting the same. An extended period of release (i.e., 50% release or less over a period of 24 hours) may be preferred in some cases.

In other instances, for example, in the case where enzymes, cells and other agents capable of acting on a substrate are used as a therapeutic agent, the therapeutic agent may remain within a copolymer matrix.

Preferred medical devices for use in conjunction with the present invention include catheters, preferably vascular catheters and more preferably balloon catheters, guide wires, balloons, filters (e.g., vena cava filters), vascular stents (including covered stents such as PTFE (polytetrafluoroethylene)-covered stents), stent grafts, cerebral stents, cerebral aneurysm filler coils (including GDC (Guglilmi detachable coils) and metal coils),vascular grafts, myocardial plugs, pacemaker leads, heart valves and intraluminal paving systems. Examples of stents include NIR stents, Medinol, Israel, RADIUS stents, Scimed Life Systems, Maple Grove, Minn., WALLSTENT stents, Boston Scientific, Natick, Mass. and SYMPHONY stents, Boston Scientific Corp., Natick, Mass. The copolymers of the present invention can also be used in composites for aneurysm fillers (e.g. polymeric mixtures of copolymer with alginates, cyanoacrylates, hydrophilic polymers and so forth). The copolymers of the present invention are further useful to incorporate cells for cell therapy and are useful for tissue engineering applications (e.g., as scaffolds for cell delivery in cardiac applications, liver regeneration, and so forth).

As noted above, the copolymer can comprise the entire device or a portion of the device, including a coating on the device or a component of a device, and so forth.

Medical devices comprising a therapeutic-agent-loaded copolymer device or device portion in accordance with the present invention can be placed in a wide variety of bodily locations for contact with bodily tissue or fluid. Some preferred placement locations include the coronary vasculature or peripheral vascular system (referred to collectively herein as the vasculature), esophagus, trachea, colon, biliary tract, urinary tract, prostate and brain.

In some instances, it may be desirable to temporarily enclose the therapeutic-agent-loaded copolymer to prevent release before the medical device reaches its ultimate placement site. As a specific example, a stent or catheter comprising therapeutic-agent-loaded copolymer can be covered with a sheath during insertion into the body to prevent premature therapeutic agent release.

Numerous techniques are available for creating medical devices and device portions from the block copolymers described herein.

For example, the fact that the block copolymers have thermoplastic character opens up a variety of standard thermoplastic processing techniques for device and device portion formation, including compression molding, injection molding, blow molding, spinning, vacuum forming and calendaring, as well as extrusion into sheets, fibers, rods, tubes and other cross-sectional profiles of various lengths. Using these and other techniques, devices such as balloons, catheters, stents and portions of devices can be made from the block copolymers.

Assuming that the therapeutic agent to be loaded is stable at processing temperatures, then it can be combined with the copolymer by extrusion prior to thermoplastic processing, producing a therapeutic-agent-loaded device or device portion. Otherwise, the therapeutic agent can be loaded after formation of the device or device portion as discussed below.

Devices or device portions can also be made using solvent-based techniques in which the block copolymer is first dissolved in a solvent and the block-copolymer solution is subsequently used to form the device or device portion. The solvent should, of course, be compatible with the block copolymer. As an example, compatible solvents for block copolymers of styrene and isobutylene include tetrahydrofuran, toluene, xylene, hexanes, heptanes, combinations of the above and the like. Preferred techniques of this nature include solvent casting, spin coating, web coating, solvent spraying, dipping, fiber forming, ink jet techniques and the like. In many cases, the solution is applied to a template, and the desired component is obtained, after solvent elimination, by simply removing the block copolymer from the template. Such techniques are particularly appropriate for forming simple objects such as sheets, tubes, cylinders and so forth.

One example of a solvent-based technique for forming a device or device portion can be found, in Example 3 of U.S. Pat. No. 5,741,331 to Pinchuk. In this example, styrene/isobutylene copolymer is dissolved in the amount of 6% solids (unless indicated otherwise, all percentages herein are weight percentages) in tetrahydrofuran and the resulting solution sprayed with an airbrush onto a rotating mandrel, which acts as a template. The environment is controlled during spraying so that the tetrahydrofuran evaporates between the sprayer and the mandrel, allowing a porous mat to be formed on the rotating mandrel. These samples are then fully dried in air and removed from the mandrel. Such a technique can be used to form, for example, vascular grafts, stent-grafts, vascular patches, hernia patches, heart valve sewing rings, and the like.

When forming devices or device portions containing a therapeutic agent using solvent-based techniques, so long as the solvent is compatible with the therapeutic agent, the therapeutic agent can be provided in the copolymer/solvent mixture, for example, in dissolved form or as a particulate suspension. Such techniques allow the therapeutic agent to be loaded concurrently with component formation.

If desired, the copolymer/solvent mixture can contain more than one solvent (for example, one solvent appropriate for the block copolymer and a different solvent appropriate for the therapeutic agent). As a specific non-limiting example, where paclitaxel is selected as a drug and where the copolymer is the triblock polystyrene-polyisobutylene-polystyrene, a solution made from toluene, tetrahydrofuran, paclitaxel and the copolymer can be used.

In cases where the therapeutic agent is not provided at the same time as device or device portion formation, if desired, the therapeutic agent can be loaded subsequent to component formation as discussed further below.

A coating is a preferred device portion that is frequently used in connection with the present invention. For example, the copolymers disclosed herein can be used to form coatings on medical device surfaces (e.g., internal or external surfaces). Such surfaces are formed from a wide variety of materials, including glass, metals, polymers, ceramics and combinations thereof.

Various techniques are available for forming coatings of the copolymer on surfaces of medical devices.

For example, coatings can be formed via thermoplastic processing, for example, by co-extruding the coating along with a medical device component.

In a preferred technique, the copolymer is first dissolved in a solvent that is compatible with the copolymer, followed by application of the copolymer solution to at least a portion of a medical device. Preferred techniques include solvent casting, spin coating, web coating, solvent spraying, dipping, ink jet and combinations of these processes. If desired (for example, to achieve a desired coating thickness), such coating techniques can be repeated or combined to build up the coated layer to the desired thickness. Coating thickness can be varied in other ways as well. For example, in one preferred process, solvent spraying, coating thickness can be increased by modification of the coating process parameters such as increasing flow rate, slowing the movement between the device to be coated and the spray nozzle, providing repeated passes, and so forth. In general the ultimate coating ranges from about 0.5 micron to 50 microns in thickness, more preferably 2 to 30 microns.

If desired, a therapeutic agent of interest can be provided at the same time as the copolymer coating, for example, by adding it to a copolymer melt during thermoplastic processing or by adding it to a copolymer solution during solvent-based processing as discussed above. Alternatively, it can be added after the coating is formed as discussed further below.

As previously noted, in some embodiments of the present invention, a therapeutic agent is provided after formation of the device or device portion. As an example of these embodiments, the therapeutic agent can be dissolved in a solvent that is compatible with both the copolymer and the therapeutic agent. Preferably, the coating or component is at most only slightly soluble in the solvent. Subsequently, the solution is contacted with the device or device portion such that the therapeutic agent is loaded (e.g., by leaching/diffusion) into the copolymer. For this purpose, the device or device portion can be immersed or dipped into the solution, the solution can be applied to the device or component, for example, by spraying, and so forth. The device or component can subsequently be dried, with the therapeutic agent remaining therein.

In several examples given above, the therapeutic agent is provided within a matrix comprising the copolymer of the present invention. The therapeutic agent can also be covalently bonded, hydrogen bonded, or electrostatically bound to the copolymer. As specific examples, nitric oxide releasing functional groups such as S-nitroso-thiols can be provided in connection with the copolymer, or the copolymer can be provided with charged functional groups to attach therapeutic groups with oppositely charged functionalities.

Alternatively, the therapeutic agent can be precipitated onto the surface of a device or device portion. This surface can be subsequently covered with a coating of copolymer (with or without additional therapeutic agent) as described above.

Hence, when it is stated herein that the block copolymer is "loaded" with therapeutic agent, it is meant that the therapeutic agent is associated with the block copolymer in a fashion like those discussed above or in a related fashion.

As previously noted, block copolymers of the present invention can be used to form entire medical devices or various portions of such medical devices. Examples include the use of the block copolymers of the present invention (1) as a single device, (2) as a combination of devices, (3) as a single device portion (such as a device component or a device coating), (4) as a combination of device portions, and so forth.

The block copolymers can also be used in connection with further auxiliary materials or device portions to achieve a desired result. Such auxiliary materials or device portions include binders, boundary layers, blending agents, and so forth.

For example, in some instances a binder may be useful for adhesion to a substrate. Examples of materials appropriate for binders in connection with the present invention include silanes, titanates, isocyanates, carboxyls, amides, amines, acrylates hydroxyls, and epoxides, including specific polymers such as EVA, polyisobutylene, natural rubbers, polyurethanes, siloxane coupling agents, ethylene and propylene oxides.

It also may be useful to coat the copolymer of the present invention (which may or may not contain a therapeutic agent) with a layer with an additional polymer layer (which may or may not contain a therapeutic agent). This layer may serve, for example, as a boundary layer to retard diffusion of the therapeutic agent and prevent a burst phenomenon whereby much of the agent is released immediately upon exposure of the device or device portion to the implant site. The material constituting the coating, or boundary layer, may or may not be the same copolymer as the loaded copolymer.

For example, the barrier layer may also be a polymer or small molecule from the following classes: polycarboxylic acids, including polyacrylic acid; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA (ethylene-vinyl acetate copolymer); polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; polypeptides, including proteins; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.); fibrin; collagen and derivatives thereof; polysaccharides such as celluloses, starches, dextrans, alginates and derivatives; and hyaluronic acid.

Copolymers and mixtures of the above are also contemplated.

A preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. In a most preferred embodiment of the invention, the polymer is a copolymer of polylactic acid and polycaprolactone.

It is also possible to form blends by adding one or more of the above or other polymers to the block copolymers of the present invention. Examples include the following:

Blends can be formed with homopolymers that are miscible with one of the block copolymer phases. For example, polyphenylene oxide is miscible with the styrene blocks of polystyrene-polyisobutylene-polystyrene copolymer. This should increase the strength of a molded part or coating made from polystyrene-polyisobutylene-polystyrene copolymer and polyphenylene oxide.

Blends can be made with added polymers or other copolymers that are not completely miscible with either of the blocks of the block copolymers of the present invention. The added polymer or copolymer may be advantageous, for example, in that it is compatible with another therapeutic agent, or it may alter the release rate of the therapeutic agent from the block copolymers of the present invention (e.g., polystyrene-polyisobutylene-polystyrene copolymer).

Blends can be made with a component such as sugar (see list above) that can be leached from the device or device portion, rendering the device or device component more porous and controlling the release rate through the porous structure.

The therapeutic-agent-loaded block copolymers are appropriate for a number of administration avenues including insertion or implantation into the body. Where the block copolymers are to be inserted or implanted for an extended period of time, biocompatibility is of concern.

The release rate of therapeutic agent from the therapeutic-agent-loaded block copolymers of the present invention can be varied in a number of ways. Examples include:

varying the molecular weight of the block copolymers,
varying the specific constituents selected for the elastomeric and thermoplastic portions of the block copolymers and the relative amounts of these constituents,
varying the type and relative amounts of solvents used in processing the block copolymers,
varying the porosity of the block copolymers,
providing a boundary layer over the block copolymer, and
blending the block copolymers of the present invention with other polymers or copolymers.

As noted above, the block copolymers used in connection with the present invention are endowed with good biocompatibility. The biocompatibility of polystyrene-polyisobutylene-polystyrene copolymers according to an embodiment of the invention is demonstrated below in connection with Example 6.

The invention is further described with reference to the following non-limiting examples.

EXAMPLE 1

Block Copolymer Synthesis.

A styrene-isobutylene-styrene block copolymer is synthesized using known techniques. As is well known by those versed in the art of cationic chemistry, all solvents and reactants must be moisture, acid and inhibitor-free. Therefore, it may be necessary, depending upon the grade of material purchased, to distill these chemicals or flow them through columns containing drying agents, inhibitor removers and the like, prior to introducing them into the reaction procedure.

Assuming that all solvents are pure and moisture- and inhibitor-free, styrene is added to a dried, airtight styrene mixing tank. The tank is initially chilled to between −19° C. (the condensation point of methyl chloride) and −31° C. (the freezing point of pure styrene) using liquid nitrogen or other heat transfer media, whereupon methyl chloride gas is condensed and added. Next, di tert-butyl-pyridine is mixed with hexanes and added to the styrene tank, followed by flushing with further hexanes. Isobutylene is then added to the styrene tank, followed by sufficient hexanes to bring total hexane weight in the styrene mixing tank to the desired amount. The temperature is then brought to about −70° C. and maintained at that temperature until used.

Hexanes are discharged into a dried, airtight reactor, containing cooling coils and a cooling jacket. The reactor with the hexanes is cooled with liquid nitrogen or other heat transfer media. Methyl chloride is condensed into the reactor by bubbling the gas through the cooled hexanes. A hindered t-butyl dicumyl ether, dimethyl phthalate and di tert-butyl-pyridine are added to the reactor, flushing with hexanes. Isobutylene is charged and condensed into the reactor by bubbling the gas thought the cooled solvent system. The temperature is maintained at about −70° C. After the isobutylene is added to the reactor, titanium tetrachloride is then charged to the reactor, flushing with hexanes, to start the reaction. After the appropriate amount of isobutylene has been added, the reaction is allowed to continue for 15 to 30 min. The contents of the styrene tank (prechilled to −60 to −70° C.) are then added to the reactor, maintaining the reactor at a temperature of about −70° C. After adding all the contents of the styrene tank, the contents of the reactor are allowed to react an additional 15 to 45 minutes, whereupon the reaction is quenched with methanol.

The reactor is then allowed to warm to room temperature, while being aware of any pressure increases, and the methyl chloride is removed from the reactor by boiling it and condensing it into a chilled collection tank. An additional amount of hexanes, or other solvent, such as tetrahydrofuran or toluene is added to the reactor to replace the removed methyl chloride. These additional solvents are used to solubilize the polymer to enable it to be drained out of the reactor, as otherwise the polymer becomes too thick to readily flow. The copolymer solution from the reactor is then precipitated in methanol (equal in weight to the initial copolymer/hexanes to be coagulated). The precipitated polymer is then poured into a sieve, the polymer removed and dried in a vacuum oven for at least 24 hours at approximately 125° C. under full vacuum.

EXAMPLE 2

Solvent-Based Coating Technique

An example of a solvent-based technique for coating a medical device, such as a stent, follows. As always, the solvent system selected for use in such a procedure will depend upon the nature of the block copolymer and therapeutic agent selected. In the case of a polystyrene-polyisobutylene-polystyrene triblock copolymer and paclitaxel therapeutic agent, a preferred solution is one containing (1) between 0–94%, preferably 94%, toluene, (2) between 5%–99%, preferably 5%, tetrahydrofuran and (3) 1% copolymer and paclitaxel combined. Such a solution can be provided by (1) mixing the paclitaxel and tetrahydrofuran, (2) adding the copolymer, (3) adding the toluene, (4) thorough mixing (e.g., overnight), and (5) filtering (e.g., through a fine filter such as a 0.22 micron filter). The solution of interest can then be placed in a syringe pump, and the fluid can be fed to a spray nozzle. The component of interest (e.g., catheter, catheter balloon, stent, stent graft, vascular graft, etc.) can be mounted onto a holding device parallel to the nozzle and, if desired, rotated (e.g., at 45 RPM) to ensure uniform coverage. Depending on the spray equipment used, either the component or spray nozzle can be moved while spraying such that the nozzle moves along the component while spraying for one or more passes. For instance, a nozzle pressurized at 15 psi for a flow rate of 6.3 mL/hr solution (polystyrene-polyisobutylene-polystyrene copolymer, paclitaxel, toluene and tetrahydrofuran), provided at a distance of 1.0 inch from the component and moved relative to the component between 0.3–0.5 mm/sec can produce a thickness of 2.5 to 4.0 microns.

EXAMPLE 3

Solvent-Based Coating Technique

In another preferred process, a solution like that above containing (1) between 0–94% toluene, (2) between 5–99% tetrahydrofuran and (3) 1% polystyrene-polyisobutylene-polystyrene copolymer and paclitaxel is sprayed with an airbrush onto a rotating medical device component, such as a stent. The environment is controlled during spraying so that the tetrahydrofuran and toluene evaporates between the sprayer and the component, allowing a porous mat loaded with a therapeutic agent to be formed on the rotating component. Spraying is stopped when the desired coating thickness is achieved.

EXAMPLE 4

Drying Process

After a component or layer has been formed using one of the above solvent-based techniques, the component or layer can be dried, for example, by placing it in a preheated oven (e.g., for 30 minutes at 65° C., followed by 3 hours at 70° C.).

EXAMPLE 5

Release Characteristics

The release rate can be varied by varying the relative amounts of drug and copolymer. FIG. 1 illustrates release rate as a function of time for NIR stents coated with polystyrene-polyisobutylene-polystyrene copolymer and paclitaxel in varying ratios. The coating formulations were made with 94% toluene and 5% tetrahydrofuran, with the remaining 1% of the formulation being made up of paclitaxel and styrene-isobutylene copolymer in respective relative amounts of 35%–65%, 32.5%–67.5%, 30%–70%, 25%–75%, 22.5%–87.5%, 20%–80% and 17.5%–83.5% with an equivalent total coating weight. Coating thickness was about 16 microns. The release rates in FIG. 1 range from a relatively rapid release in connection with the highest paclitaxel value (35%) to a relatively slow release at the lowest value (17.5%).

EXAMPLE 6

Biocompatibility

For this investigation, the following are provided: (1) a bare stainless steel NIR (Medinol, Israel) stent; (2) a NIR stent with a coating of traditional "biostable" polycarbonate urethane polymer (Chronoflex AL, CardioTech Inc., Woburn Mass.); (3) a NIR stent with a coating of a traditional "biodegradable" copolymer of polylactic acid ("PLA") and polyglycolic acid ("PGA") (Birmingham Polymers, Birmingham, Ala.); and (4) a NIR stent with a coating of polystyrene-polyisobutylene-polystyrene copolymer in accordance with the present invention.

These stents were implanted in a porcine coronary artery. After 28 days, the stent was harvested from the animal and examined for both stenosis (neointimal thickening) and inflammation. Stenosis was measured angiographically. Inflammation was measured by blinded observers based on microscopic inspection of sections retrieved from the porcine artery. Inflammation values of 1 to 4 were assigned, with 1 representing the minimal inflammation and 4 representing maximal inflammation. The results are presented in the following table:

| Coating | Stenosis (%) | Inflammation |
|---|---|---|
| None (Bare Stent) | 43 ± 7 | 2.6 ± 0.7 |
| Polycarbonate urethane | 75 ± 15 | 3.9 ± 0.8 |
| Polystyrene-polyisobutylene-polystyrene copolymer | 47 ± 9 | 1.5 ± 0.5 |
| PLA/PGA copolymer | — | — |

As can be seen from this table, stenosis and inflammation were significantly higher with the stents coated with traditional polycarbonate urethane polymer than was observed than with the bare stent or with the stents coated with polystyrene-polyisobutylene-polystyrene copolymer.

FIGS. 2A, 2B, 2C and 2D show representative histology of the sections from the stented arteries. The extent of inflammation and neointimal thickness was much more pronounced in FIG. 2C (appearance of the vessel associated with the traditional "biostable" polyurethane-carbonate-coated stent) and FIG. 2D (traditional "biodegradable" PLA/PGA copolymer), than in FIG. 2A (bare stent) or FIG. 2B (polystyrene-polyisobutylene-polystyrene coated stent).

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A composition for delivery of a therapeutic agent comprising:
   a biocompatible block copolymer comprising one or more polyolefin elastomeric blocks and one or more thermoplastic blocks selected from vinyl aromatic blocks and methacrylate blocks; and
   a therapeutic agent, said block copolymer being loaded with said therapeutic agent.

2. The composition of claim 1, wherein said one or more polyolefin elastomeric blocks comprise an isobutylene monomer and wherein said one or more thermoplasic blocks comprise one or more monomers selected from styrene and α-methylstyrene.

3. The composition of claim 1, wherein said block copolymer is of the formula X—(AB)$_n$, where A is a polyolefin block, B is a vinyl aromatic block or a methacrylate block, n is a positive whole number and X is a seed molecule.

4. The composition of claim 3, wherein A is a polyolefin block of the general formula —(CRR'—CH$_2$)$_n$—, where R and R' are linear or branched aliphatic groups or cyclic aliphatic groups and B is a methacrylate polymer block.

5. The composition of claim 4, wherein B comprises one or more monomers selected from methylmethacrylate, ethylmethacrylate and hydroxyethyl methacrylate.

6. The composition of claim 3, wherein A is a polyolefin block of the general formula —(CRR'—CH$_2$)$_n$—, where R and R' are linear or branched aliphatic groups or cyclic aliphatic groups and wherein B is a vinyl aromatic polymer block.

7. The composition of claim 6, wherein said polyolefin block comprises an isobutylene monomer and wherein said vinyl aromatic polymer block comprises one or more monomers selected from styrene and α-methylstyrene.

8. The composition of claim 6, wherein the amount of polyolefin blocks ranges from between 95 and 45 mol % of the block copolymer.

9. The composition of claim 6, wherein the molecular weight of the block copolymer ranges from 80,000 to 300,000 Daltons.

10. The composition of claim 6, wherein the molecular weight of the polyolefin blocks ranges from 60,000 to 200,000 and the molecular weight of the vinyl aromatic polymer blocks ranges from 20,000 to 100,000.

11. The composition of claim 1, wherein said loaded block copolymer comprises 0.1 to 70 wt% therapeutic agent.

12. The composition of claim 6, wherein said loaded block copolymer comprises 0.1 to 70 wt% therapeutic agent.

13. The composition of claim 7, wherein said loaded block copolymer comprises 0.1 to 70 wt % therapeutic agent.

14. A medical device, at least a portion of which is insertable or implantable into the body of a patient, comprising:
   a block copolymer comprising one or more polyolefin elastomeric blocks and one or more thermoplastic blocks selected from vinyl aromatic blocks and methacrylate blocks; and
   a therapeutic agent, said block copolymer being loaded with said therapeutic agent.

15. The medical device of claim 14, wherein said one or more polyolefin elastomeric blocks comprise an isobutylene monomer and wherein said one or more thermoplastic block comprise one or more monomers selected from styrene and α-methylstyrene.

16. The medical device of claim 14, wherein said block copolymer is of the formula X—(AB)$_n$, where A is a polyolefin block, B is a vinyl aromatic block or a methacrylate block, n is a positive whole number and X is a seed molecule.

17. The medical device of claim 16, wherein A is a polyolefin block of the general formula —(CRR'—CH$_2$)$_n$—, where R and R'are linear or branched aliphatic groups or cyclic aliphatic groups, and B is a methacrylate polymer block.

18. The medical device of claim 16, wherein A is a polyolefin block of the general formula —(CRR'—CH$_2$)$_n$—, where R and R' are linear or branched aliphatic groups or cyclic aliphatic groups and wherein B is a vinyl aromatic polymer block.

19. The medical device of claim 18, wherein said polyolefin block comprises an isobutylene monomer and wherein said vinyl aromatic polymer block comprises one or more monomers selected from styrene and α-methylstyrene.

20. The medical device of claim 14, wherein only a portion of said medical device comprises said block copolymer.

21. The medical device of claim 20, wherein said portion of said medical device is a coating on said medical device.

22. The medical device of claim 14, wherein therapeutic agent is released over an extended period after implantation in a patient.

23. The medical device of claim 14, wherein the medical device is adapted such that at least a portion of said block copolymer is exposed to bodily fluid upon insertion or implantation in the body.

24. The medical device of claim 14, wherein the medical device is adapted such that at least a portion of said block copolymer is exposed to tissue upon insertion or implantation in the body.

25. The medical device of claim 14, wherein said medical device is a catheter, guide wire, balloon, filter, stent, stent graft, vascular graft, vascular patch, shunt or intraluminal paving system.

26. The medical device of claim 14, wherein said medical device is adapted for implantation or insertion into the coronary vasculature, peripheral vascular system, esophagus, trachea, colon, biliary tract, urinary tract, prostate or brain.

27. The medical device of claim 14, wherein said medical device is a stent.

28. The medical device of claim 21, wherein said coating ranges from about 0.1 to 50 microns in thickness.

29. The medical device of claim 14, wherein said therapeutic agent is selected from one or more of the group consisting of an anti-thrombotic agent, an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogneous vasoactive mechanisms.

30. The medical device of claim 14, wherein said therapeutic agent is selected from anti-sense. DNA, anti-sense RNA, DNA coding for anti-sense RNA, DNA coding for RNA or rRNA, DNA coding for angiogenic factors, DNA coding for cell cycle inhibitors, DNA coding for cell proliferation inhibition agents, and DNA coding for bone morphogenic proteins.

31. The medical device of claim 14, wherein said therapeutic agent is selected from autologous cells, allogeneic cells and xenogeneic cells.

32. A method of treatment comprising implanting or inserting the device of claim 14 into a patient such that said therapeutic agent is released in said patient over an extended period.

33. A medical device, at least a portion of which is insertable or implantable into the vasculature of a patient, comprising:

a block copolymer portion of the formula X—(AB)$_n$, wherein A is a polyolefin block of the general formula —(CRR'—CH$_2$)$_n$—, where R and R' are linear or branched aliphatic groups or cyclic aliphatic groups, B is a vinyl aromatic polymer block, n is a positive whole number and X is a seed molecule; and a therapeutic agent, said block copolymer being loaded with said therapeutic agent, and said therapeutic agent selected from of one or more of the group consisting of an anti-thrombotic agent, an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promotor, a vascular cell growth inhibitor, a cholesterol-lowering agent, a vasodilating agent, and an agent that interferes with endogenous vascoactive mechanisms.

34. The medical device of claim 33, wherein said polyolefin block comprises an isobutylene monomer and wherein said vinyl aromatic polymer block comprises one or more monomers selected from styrene and α-methylstyrene.

35. The medical device of claim 33, wherein said medical device is selected from a catheter, guide wire, balloon, filter, stent, stent graft, vascular graft, vascular patch or intraluminal paving system.

36. The medical device of claim 33, wherein said block copolymer is in the form of a coating over at least a portion of said medical device.

37. The medical device of claim 34, wherein said block copolymer is in the form of a coating over at least a portion of a medical device selected from the group consisting of a balloon, a stent, a shunt, a catheter, and a filter wherein said therapeutic agent is paclitaxel.

38. The medical device of claim 37, wherein said coating ranges from 0.1 to 40 microns in thickness.

39. The medical device of claim 37, wherein said loaded block copolymer portion comprises 0.1 to 75 wt % paclitaxel.

40. The medical device of claim 37, wherein the molecular weight of the polyisobutylene blocks ranges from 60,000 to 200,000 and the molecular weight of the polystyrene or poly-α-methylstyrene blocks ranges from 20,000 to 100,000.

41. A coated medical device comprising:

an intravascular or intervascular medical device; and a coating over at least a portion of said intravascular or intervascular medical device, said coating comprising a biocompatible block copolymer comprising one or more polyolefin elastomeric blocks and one or more thermoplastic blocks selected from vinyl aromatic block and methacrylate blocks.

42. The coated medical device of claim 41, where said one or more polyolefin elastomeric block comprise an isobutylene monomer and wherein said one or more thermoplastic blocks comprise one or more monomers selected from styrene and α-methylstyrene.

43. The coated medical device of claim 41, wherein said block copolymer is of the formula X—(AB)$_n$, where A is a polyolefin block, B is a vinyl aromatic block or a methacrylate block, n is a positive whole number and X is a catalyst seed molecule.

44. The coated medical device of claim 43, wherein A is a polyolefin block of the general formula —(CRR'—CH$_2$)$_n$—, where R and R' are linear or branched aliphatic groups or cyclic aliphatic groups, and B is a methacrylate polymer block.

45. The coated medical device of claim 44, wherein B comprises one or more monomers selected from methylmethacrylate, ethylmethacrylate and hydroxyethyl methacrylate.

46. The coated medical device of claim 43, wherein A is a polyolefin block of the general formula —(CRR'—CH$_2$)$_n$—, where R and R' are linear or branched aliphatic groups or cyclic aliphatic groups and wherein B is a vinyl aromatic polymer block.

47. The coated medical device of claim 46, wherein said polyolefin block comprises an isobutylene monomer and wherein said vinyl aromatic polymer block comprises one or more monomers selected from styrene and α-methylstyrene.

48. The coated medical device of claim 46, wherein the amount of polyolefin blocks ranges from between 95 and 45 mol % of the block copolymer.

49. The coated medical device of claim 46, wherein the molecular weight of the block copolymer ranges from 80,000 to 300,000 Daltons.

50. The coated medical device of claim 46, wherein the molecular weight of the polyolefin blocks ranges from 60,000 to 200,000 Daltons and the molecular weight of the vinyl aromatic polymer blocks ranges from 20,000 to 100,000 Daltons.

51. The device of claim 41, wherein said intravascular or intervascular medical device is selected from a balloon, a stent, a shunt, a catheter, a stent graft, a vascular graft, a vascular patch, and a filter.

52. The medical device of claim 14, further comprising a polymer or copolymer of one or more of the following: a polycarboxylic acid, a cellulose acetate polymer, a cellulose nitrate polymer, a gelatin, a polyvinylpyrrolidone, a cross-linked polyvinylpyrrolidone, a polyanhydride, a polyamide, a polyvinyl alcohol, a polyvinyl ether, a polyvinyl aromatic, a polyethylene oxide, a glycosaminoglycan, a polysaccharide, a polyester, a polyacrylamide, a polyether, a polyether sulfone, a polycarbonate, a polyalkylene, a halogenated polyalkylene, a polyurethane, a polyorthoester, a polypeptide, a silicone, a siloxane polymer, a polylactic acid, a polyglycolic acid, a polycaprolactone, a polyhydroxybutyrate valerate, a fibrin, a collagen, a collagen derivative or a hyaluronic acid.

53. The medical device of claim 52, wherein said polymer or copolymer is selected from a polyacrylic acid, an ethylene-vinyl acetate copolymer, and a copolymer of polylactic acid and polycaprolactone.

54. The medical device of claim 52, wherein said polymer or copolymer is blended with said biocompatible block copolymer.

55. The medical device of claim 52, wherein said polymer or copolymer is provided in a layer that does not contain said biocompatible block copolymer.

56. The medical device of claim 19, wherein the molecular weight of the polyisobutylene blocks ranges from 60,000 to 200,000 and the molecular weight of the polystyrene or poly -α-methylstyrene blocks ranges from 20,000 to 100,000.

57. The medical device of claim 19, wherein said therapeutic agent is paclitaxel.

58. The medical device of claim 25, wherein said polyolefin block comprises an isobutylene monomer and wherein said vinyl aromatic block comprises one or more monomers selected from polystyrene and poly-α-methylstyrene.

59. The medical device of claim 58, wherein said therapeutic agent is paclitaxel.

* * * * *

UNITED STATES PATENT AND TRADEMARK OFFICE
CERTIFICATE OF CORRECTION

PATENT NO.    : 6,545,097 B2
DATED         : April 8, 2003
INVENTOR(S)   : Leonard Pinchuk et al.

It is certified that error appears in the above-identified patent and that said Letters Patent is hereby corrected as shown below:

<u>Title page,</u>
Item [57], ABSTRACT,
Line 3, after "intervascular" delete -- a --.

<u>Column 1,</u>
Line 44, after "endogenous" change "vascoactive" to -- vasoactive --.

<u>Column 7,</u>
Line 44, after "endogenous" change "vascoactive" to -- vasoactive --.
Line 57, after "factor," change "a" to -- α --.

<u>Column 18,</u>
Line 48, after "gas", change "thought" to -- through --.

<u>Column 21,</u>
Line 3, after "thermoplastic", change "block" to -- blocks --.
Line 5, after "polyolefin", change "clastomeric" to -- elastomeric --.

<u>Column 22,</u>
Line 39, before "trachea", change "csophagus" to -- esophagus --.
Line 57, before "or rRNA", change "RNA" to -- tRNA --.

<u>Column 23,</u>
Line 20, after "endogenous" change "vascoactive" to -- vasoactive --.
Line 54, before "and", change "block" to -- blocks --.

UNITED STATES PATENT AND TRADEMARK OFFICE
CERTIFICATE OF CORRECTION

PATENT NO. : 6,545,097 B2
DATED : April 8, 2003
INVENTOR(S) : Leonard Pinchuk et al.

It is certified that error appears in the above-identified patent and that said Letters Patent is hereby corrected as shown below:

Column 23 cont'd,
Line 56, after "elastomeric", change "block" to -- blocks --.

Signed and Sealed this

Fifteenth Day of July, 2003

JAMES E. ROGAN
*Director of the United States Patent and Trademark Office*

UNITED STATES PATENT AND TRADEMARK OFFICE
Certificate

Patent No. 6,545,097 B2            Patented: April 8, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Leonard Pinchuk, Miami, FL; Sepideh Nott, Weston, MA; Marlene Schwarz, Aburndale, MA; Kalpana Kamath, Natick, MA; and Ni Ding, San Jose, CA.

Signed and Sealed this Fifteenth Day of February 2005.

JAMES J. SEIDLECK
                                             *Supervisory Patent Examiner*
                                                       Art Unit 1711

UNITED STATES PATENT AND TRADEMARK OFFICE
CERTIFICATE OF CORRECTION

PATENT NO.        : 6,545,097 B2
APPLICATION NO. : 09/734639
DATED             : April 8, 2003
INVENTOR(S)       : Leonard Pinchuk et al.

It is certified that error appears in the above-identified patent and that said Letters Patent is hereby corrected as shown below:

Specification, Col. 3, line 32, change "polyglycolic acid ("PGA")" to

-- polycaprolactone ("PCL") --.

Specification, Col. 20, line 24, change first words "polyglycolic acid ("PGA")" to -- polycaprolactone ("PCL") --.

Specification, Col. 20, line 46, change "PLA/PGA copolymer" to -- PLA/PCL copolymer --.

Specification, Col. 20, line 60, change first word "PGA" to -- PCL --.

Signed and Sealed this

Sixth Day of February, 2007

JON W. DUDAS
*Director of the United States Patent and Trademark Office*